United States Patent [19]

Töpfl

[11] Patent Number: 4,684,736

[45] Date of Patent: Aug. 4, 1987

[54] BISIMIDAZOLIUM SALTS

[75] Inventor: Rosemarie Töpfl, Dornach, Switzerland

[73] Assignee: Ciba-Geigy Corporation, Ardsley, N.Y.

[21] Appl. No.: 794,936

[22] Filed: Nov. 4, 1985

[30] Foreign Application Priority Data

Jan. 25, 1985 [CH] Switzerland .............................. 351/85

[51] Int. Cl.$^4$ ................... C07D 233/61; C07D 233/72
[52] U.S. Cl. ........................................ 548/309; 8/573; 548/336
[58] Field of Search ............................... 548/309, 336

[56] References Cited

U.S. PATENT DOCUMENTS

| | | | |
|---|---|---|---|
| 2,043,164 | 6/1936 | Gränacher | 548/326 |
| 3,435,049 | 3/1969 | Hoffer | 548/336 |
| 3,853,907 | 12/1974 | Edwards | 548/336 |
| 3,991,202 | 11/1976 | Janssen et al. | 548/336 |
| 4,035,145 | 7/1977 | Gipp et al. | 8/74 |
| 4,468,228 | 8/1984 | Dvorsky et al. | 548/336 |
| 4,499,282 | 2/1985 | Dvorsky et al. | 548/336 |

Primary Examiner—Henry R. Jiles
Assistant Examiner—Kurt G. Briscoe
Attorney, Agent, or Firm—Edward McC. Roberts; Meredith C. Findlay; Kevin T. Mansfield

[57] ABSTRACT

The invention relates to bisimidazolium salts whose imidazole moieties are linked to each other through a bridge in the 1-position and which contain, in the 3-position, fibre-reactive groups formed by the addition of epihalohydrin.

These bisimidazolium salts are particularly suitable for improving the yield and wetfastness properties of dyeings or prints which are produced on cellulosic fabrics with anionic dyes, for example with reactive or direct dyes.

16 Claims, No Drawings

# BISIMIDAZOLIUM SALTS

The present invention relates to bisimidazolium salts, to their preparation and to the use thereof as assistants for producing dyeings or prints on cellulosic fabric with anionic dyes.

The bisimidazolium salts of this invention are water-soluble bisimidazolium compounds, the imidazole moieties of which are linked to each other through a bridge in the 1-position and which contain, in the 3-position, fibre-reactive groups formed by the addition of epihalohydrin.

Preferred bisimidazolium salts are those of the formula $$\left[ X_1-N\underset{\underset{R_1}{Y}}{\overset{A}{=\!=\!=}}N-Q-N\underset{\underset{R_2}{Y}}{\overset{B}{=\!=\!=}}N-X_2 \right]_n^{2\oplus} \quad 2Y^{n\ominus} \quad (1)$$

wherein

Q is a divalent aliphatic hydrocarbon radical of 4 to 12 carbon atoms which may be interrupted in the chain by oxygen or a hydantoin group and which is unsubstituted or substituted by hydroxyl groups, $X_1$ and $X_2$, each independently of the other, are the $$-CH_2-CH\underset{O}{-\!-\!-}CH_2 \quad \text{or preferably}$$

$$-CH_2-\underset{\underset{OH}{|}}{CH}-CH_2-Hal \text{ group,}$$

Hal is a halogen atom, $R_1$ and $R_2$, each independently of the other, are hydrogen, phenyl or an aliphatic radical, n is 1 or 2, and $Y^\ominus$ is an anion of a strong inorganic or organic acid, and the imidazole rings A and B, each independently of the other, are unsubstituted or substituted by lower alkyl which is in turn unsubstituted or substituted by halogen, hydroxyl or cyano.

Halogen as moiety of all substituents throughout this specification denotes for example bromine, fluorine, iodine or, preferably, chlorine.

The imidazole moieties, including the fibre-reactive groups $X_1$ and $X_2$, are preferably identical and $X_1$ and $X_2$ are in particular halohydrin groups of the formula $$-CH_2-\underset{\underset{OH}{|}}{CH}-CH_2-Hal_1 \quad (1a)$$

wherein $Hal_1$ is bromine or preferably chlorine.

As aliphatic radical, $R_1$ and $R_2$ may be saturated or unsaturated, straight chain or branched and may contain up to 23 carbon atoms. $R_1$ and $R_2$ are with advantage a $C_1$-$C_{23}$alkyl radical.

Examples of such alkyl radicals are: methyl, ethyl, n-propyl, isopropyl, n-butyl, isobutyl, n-amyl, isoamyl, hexyl, heptyl, octyl, isooctyl, nonyl, isononyl, undecyl, dodecyl, tridecyl, pentadecyl, heptadecyl, nonadecyl, heneicosyl or tricosyl.

Preferably $R_1$ and $R_2$ are hydrogen, phenyl, lower alkyl, undecyl or heptadecyl.

Lower alkyl throughout denotes those groups or moieties which contain 1 to 5, preferably 1 to 3, carbon atoms, e.g. methyl, ethyl, n-propyl, isopropyl, n-butyl, isobutyl, tert-butyl, n-amyl, isoamyl or tert-amyl.

Substituted lower alkyl radicals are in particular haloalkyl, cyanoalkyl or hydroxyalkyl, each containing 2 to 4 carbon atoms, for example 2-chloroethyl, 2-cyanoethyl, 2-hydroxyethyl or 3-hydroxy-propyl.

The aliphatic hydrocarbon chain in the bridge Q preferably contains 6 to 10 carbon atoms.

The hydantoin group which may be present in the bridge Q is linked through the nitrogen atoms to the hydrocarbon chain and in the α-position may be unsubstituted or substituted by one or two lower alkyl groups, preferably methyl.

Preferably Q is a divalent $C_6$-$C_{10}$alkylene radical which may be interrupted in the chain by oxygen or a hydantoin group and which is unsubstituted or substituted by hydroxyl groups, and is most preferably a $C_6$-$C_{10}$alkylene radical which is interrupted by an oxygen atom and substituted by hydroxyl groups.

The hydantoin group is preferably derived from hydantoin, α-methylhydantoin or, most preferably, from α-dimethylhydantoin. Particularly preferred bridges Q are $$-CH_2-\underset{\underset{OH}{|}}{CH}-CH_2- \text{ and}$$

$$-CH_2-\underset{\underset{OH}{|}}{CH}-CH_2-\underset{}{N}\underset{\underset{\underset{O}{\|}}{C}}{\overset{\overset{CH_3\ \ CH_3}{\underset{|}{C}\!-\!-\!-\!C=O}}{\phantom{X}}}N-CH_2-\underset{\underset{OH}{|}}{CH}-CH_2-.$$

Possible anions $Y^\ominus$ are anions of inorganic acids such as the chloride, bromide, fluoride, iodide, sulfate or phosphate ion, as well as anions of organic acids, for example of aromatic or aliphatic sulfonic acids, e.g. the benzenesulfonate, p-toluenesulfonate, chlorobenzenesulfonate, methane- or ethanesulfonate ion, and also the anions of lower carboxylic acids such as the acetate, propionate or oxalate ion.

$Y^\ominus$ is preferably the chloride, bromide or sulfate ion.

Interesting bisimidazolium salts are those of the formula $$\left[ \begin{array}{c} CH_2-N\underset{\underset{R_3}{Y}}{\overset{D}{=\!=\!=}}N-Q_1-N\underset{\underset{R_3}{Y}}{\overset{D}{=\!=\!=}}N-CH_2 \\ | \qquad\qquad\qquad\qquad\qquad\qquad\qquad | \\ CH-OH \qquad\qquad\qquad\qquad\qquad CH-OH \\ | \qquad\qquad\qquad\qquad\qquad\qquad\qquad | \\ CH_2-Hal_1 \qquad\qquad\qquad\qquad\qquad CH_2-Hal_1 \end{array} \right]_n^{2\oplus} \quad 2Y_1^{n\ominus} \quad (2)$$

wherein $Hal_1$, n and $Y^\ominus$ have the given meanings, $Q_1$ is a $C_6$-$C_{10}$alkylene radical which is unsubstituted or substituted by hydroxyl groups and which may be interrupted in the chain by oxygen or by a hydantoin group which is attached to the N-atoms and is unsubstituted or substituted in the α-position by methyl, and R₃ is hydrogen, phenyl or $C_1$-$C_{17}$alkyl, and the ring D is unsubstituted or substituted by methyl or ethyl.

Particularly interesting bisimidazolium salts are those of the formula

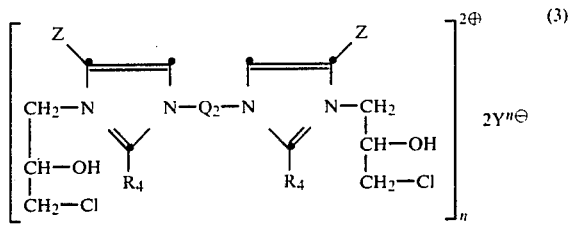

wherein

Q₂ is a $C_6$-$C_{10}$alkylene radical which is unsubstituted or substituted by hydroxyl groups and which may be interrupted in the chain by oxygen or by a hydantoin group which is attached to the N-atoms and is substituted in the α-position by methyl, R₄ is hydrogen, phenyl or $C_1$-$C_{11}$alkyl, Z is hydrogen or methyl, n is 1 or 2, and $Y_1^{\ominus}$ is the chloride or sulfate ion.

Among these bisimidazolium salts of formula (3), those compounds are particularly preferred in which Q₂ is a $C_6$-$C_{10}$alkylene radical which is interrupted in the chain by oxygen and which is substituted by hydroxyl groups, R₄ is hydrogen or methyl, Z is hydrogen, n is 1 or 2, and $Y_1^{\ominus}$ is the chloride or sulfate ion.

The preparation of the bisimidazolium salts is carried out in a manner known per se. Preferably the procedure comprises reacting 1 mole of a bisimidazole of the formula

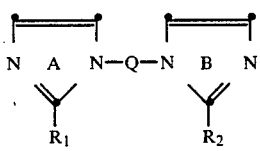

wherein A, B, Q, R₁ and R₂ have the given meanings, or preferably the acid salt thereof with e.g. hydrochloric acid or sulfuric acid, with 2 moles of an epihalohydrin, e.g. epibromohydrin, β-methylepibromohydrin or, preferably, epichlorohydrin.

The reaction conditions for the preparation of the bisimidazolium salts must be so chosen that a premature exchange of mobile substituents does not occur as a consequence of too high pH values of the reaction medium or of a too high temperature. The reaction is therefore preferably conducted in a dilute aqueous medium under as mild pH and temperature conditions as possible, conveniently in the temperature range from 30° to 95° C. and in the pH range from 5 to 8, preferably from 5.5 to 7. To obtain the desired pH value, a hydrohalic acid such as hydrochloric acid, or sulfuric acid, may be added.

The reaction of the bisimidazole compounds with the epihalohydrin can also be carried out by heating the components to a temperature in the range from 40° to 95° C., if desired also in an organic solvent.

Suitable organic solvents that form the reaction medium are aliphatic lower alcohols such as methanol, ethanol, propanol or isopropanol; cycloaliphatic or preferably aromatic hydrocarbons such as cyclohexane, benzene, toluene or xylene; chlorinated hydrocarbons such as ethylene chloride, tetrachloroethylene; cyclic ethers such as dioxane or tetrahydrofuran; dimethylsulfoxide; or nitriles of aliphatic monocarboxylic acids, e.g. acetonitrile, propionitrile or butyronitrile. Mixtures of these solvents may also be used.

The starting bisimidazoles of formula (4) can be obtained in high yield and purity by reacting 1 mole of an imidazole of each of formulae

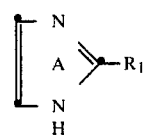

and

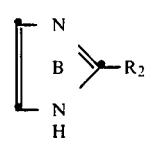

or two moles of the same imidazole, with a compound that introduces Q and which contains two functional groups, for example an olefin dioxide or a diepoxy compound such as a 1,3-diglycidylhydantoin or an α,ω-alkanediol diglycidyl ether.

Examples of suitable imidazole components for the preparation of the bisimidazole compounds of formula (4) are: imidazole, 2-methylimidazole, 2-ethylimidazole, 2-isopropylimidazole, 2,4-dimethylimidazole, 2-ethyl-4-methylimidazole, 2-phenylimidazole, 2-heptylimidazole, 2-phenyl-4-methylimidazole, 2-undecylimidazole, 4-methyl-2-undecylimidazole, 4,5-dimethyl-2-undecylimidazole, 4-ethyl-2-undecylimidazole, 2-heptadecylimidazole, 4-cyanoethyl-2-methylimidazole, 4-cyanoethyl-2-undecylimidazole and the corresponding acid salts.

2-Methylimidazole, 2-phenylimidazole and, in particular, imidazole, are especially preferred.

Examples of compounds that introduce Q and which contain two functional groups are: butadiene dioxide, 1,3-diglycidylhydantoin, 1,3-diglycidyl-4-methylhydantoin or 1,3-diglycidyl-4-dimethylhydantoin and, preferably, 1,4-butanediol diglycidyl ether.

The bisimidazolium salts of this invention are particularly suitable assistants for improving the colour yield and the wetfastness properties of dyeings and prints which are obtained on cellulosic fabrics with anionic dyes.

The treatment of the cellulosic fabric with the cationic bisimidazole compound is preferably effected continuously by a pad process in which the cellulosic fabric is impregnated with the fixing agent, e.g. by padding, and then subjected to a fixation process. This application may be made before, during or after dyeing. It is preferred to carry out the treatment after or, most preferably, during dyeing. The aftertreatment may be applied to dyeings as well as to colour prints.

The impregnating step may be carried out in the temperature range from 20° to 70° C., but preferably at room temperature. The fixation step can be carried out by a steam process, a thermosol process, a microwave treatment or by a hot dwell or cold pad batch process.

In the steaming process, the textile fabrics padded with the treatment liquor are subjected to a fixation treatment in a steamer with steam or superheated steam, advantageously in the temperature range from 98° to 130° C., preferably from 102° to 110° C.

The thermosol fixation can be effected after or without intermediate drying, e.g. in the the temperature range from 100° to 210° C. The thermosol fixation is preferably carried out in the temperature range from 120° C. to 210° C., most preferably from 140° to 180° C., and after first drying the padded or printed goods at 80° to 120° C. Depending on the temperature, the thermosol fixation may take from 20 seconds to 5 minutes, preferably from 30 to 180 seconds.

The thermofixation may also be effected with microwaves. In this method, the goods are conveniently rolled up and treated in a chamber with microwaves after they have been impregnated with the treatment liquor and pinched-off to remove excess liquor. This microwave treatment may take from 2 to 120 minutes, but 2 to 15 minutes preferably suffice. By microwaves are meant electromagnetic waves (radio waves) in the frequency range from 300 to 100,000 mHz, preferably 1000 to 30,000 mHz.

In the hot dwell process, the padded or printed goods are left in the moist state for e.g. 15 to 120 minutes, advantageously in the temperature range from 85° to 102° C. In this case, the impregnated goods can be preheated to 85°–120° C. by an infra-red treatment. The dwell temperature is preferably from 90° to 100° C.

The fixation stage can also be effected by the cold pad batch process, in which the padded or printed goods, which are preferably rolled up, are stored at room temperature (15°–30° C.) for e.g. 3 to 24 hours. If desired, the goods may also be stored at slightly elevated temperature (30°–80° C.).

Treatment with the bisimidazolium salts is preferably carried out by the cold pad batch process and, in particular, during dyeing.

The continous treatment after dyeing is preferably carried out by padding the dyed or printed fabric followed by the subsequent thermosol fixation.

The treatment of the textile fabrics with the bisimidazolium salts can also be carried out by the exhaust process before or after dyeing, but preferably during dyeing. In this case, treatment may be effected in the temperature range from 20° to 135° C., preferably from 40° to 100° C. The liquor to goods ratio may be chosen within a wide range, for example from 1:2.5 to 1:100, preferably from 1:5 to 1:40.

In the exhaust process, the treatment liquors preferably contain the bisimidazolium salts in an amount of 1 to 25% by weight, most preferably from 2 to 15% by weight, based on the weight of the cellulosic fabric, whereas padding liquors or printing pastes preferably contain them in an amount of 1 to 100 g/l, most preferably 10 to 50 g/l, with the goods being conveniently pinched-off to a pick-up of 60 to 120% by weight in the pad process.

The dyes employed are the substantive dyes or reactive dyes conventionally used for dyeing cellulosic fabrics. Suitable substantive dyes are the customary direct dyes, for example the "Direct Dyes" listed in the Colour Index, 3rd edition (1971), Vol. 2, pp. 2005-2478.

By reactive dyes are meant the customary dyes which form a chemical bond with cellulose, for example the "Reactive Dyes" listed in the Colour Index, Vol. 3 (3rd edition, 1971) on pages 3391–3560 and in Vol. 6 (revised 3rd edition, 1975) on pages 6268–6345. When dyeing and carrying out the treatment with the bisimidazolium salts simultaneously, the amount of dye will normally depend on the desired tinctorial strength and in the continuous process is conveniently from 0.1 to 100 g per litre of liquor, preferably from 5 to 60 g per litre of liquor. In the exhaust process, the amount of dye is advantageously from 0.1 to 10% by weight, preferably from 1 to 6% by weight.

Besides the cationic bisimidazolium salts, the liquors employed in the process of this invention additionally contain alkalies such as sodium carbonate, sodium bicarbonate, sodium hydroxide, disodium phosphate, trisodium phosphate, borax, aqueous ammonia or alkali donors such as sodium trichloroacetate or sodium formate.

The pH of the treatment and dye liquors is accordingly usually in the range from 8 to 13.5, preferably from 8.5 to 13.

If desired, the liquors may also contain urea, glycerol, sodium formate, electrolytes such as sodium chloride or sodium sulfate, alkali-resistant wetting agents, homopolymers or copolymers of acrylamide or methacrylamide, or the graft polymers described in European published patent application No. EP-A-111454, as well as thickeners, e.g. alginates, starch ethers or carob seed gum ether.

The bisimidazolium salts of this invention are suitable for the treatment of textiles which consist of cellulose or which contain cellulose.

Suitable cellulosic fabric is that made from regenerated or, in particular, natural cellulose, for example viscose rayon, viscose silk, cellulose acetate, hemp, jute or, preferably, cotton, as well as blends, e.g. polyamide/cotton or, in particular, polyester cotton blends, in which the polyester component may be predyed or cross-dyed.

The textile fabric may be in any form, for example yarn, hanks, woven fabrics, knitted fabrics, felt, but is preferably in the form of textile planar structures such as woven or knitted goods which consist wholly or partly of native, regenerated or modified cellulose.

The bisimidazolium salts of this invention give level and strong dyeings which, compared with those obtained with known processes, are distinguished by improved colour yield. In particular, dyeings and prints with substantially improved wetfastness properties are obtained on cellulosic fabric with reactive dyes as well as with substantive dyes. In addition, the use of the bisimidazolium salts of this invention does not impair the decrease in tear resistance of the dyeings.

In the following Preparatory and Use Examples, percentages are by weight unless otherwise indicated. The amounts of dye refer to commercial, i.e. diluted, product, and amounts of auxiliaries refer to pure substance. The 5-digit Colour Index (C.I.) numbers refer to the 3rd. edition of the Colour Index.

PREPARATORY EXAMPLES

EXAMPLE 1

177 g of a bisimidazole (50% in water) of the formula

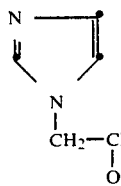 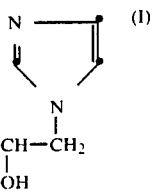

are mixed with 12.7 g of 96% sulfuric acid and 33.5 g of water. Then 46.25 g of epichlorohydrin are added dropwise at 60° C. to the solution so obtained, the temperature rising to about 70° C. The reaction mixture is subsequently stirred for 5½ hours at 70°–75° C. after which reaction time the amine number and epoxy number are both 0. The solution is evaporated to dryness, affording 146 g of a bisimidazolium salt of the formula

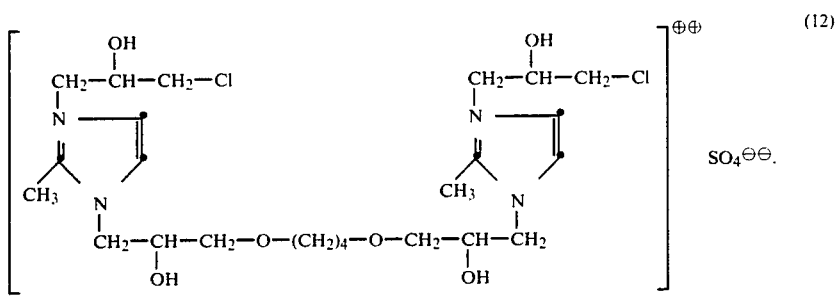

The starting bisimidazole of formula (I) is prepared as follows:

34 g of imidazole are dissolved in 88.5 g of water and the resultant solution is warmed to 45° C. Then 54.5 g of butanediol diglycidyl ether are added dropwise over 15 minutes, the temperature rising to 60° C. The reaction mixture is stirred for 25 minutes at this temperature, affording 177 g of a clear 50% solution of the bisimidazole of formula (I). The epoxide content is 0.

EXAMPLE 2

184 g of a bisimidazole (52% in water) of the formula

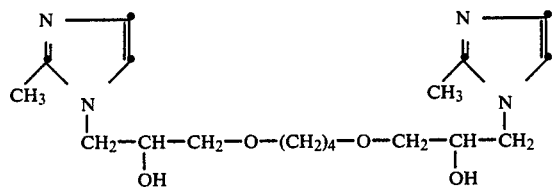

are mixed with 12.7 g of 96% sulfuric acid and 33.5 g of water. Then 46.25 g of epichlorohydrin are added dropwise at 60° C. to the solution so obtained, the temperature rising to about 70° C. The reaction mixture is subsequently stirred for 5½ hours at 70°–75° C. and after this time the amine number and epoxy number are both 0. The solution is evaporated to dryness, affording 154 g of a bisimidazolium salt of the formula

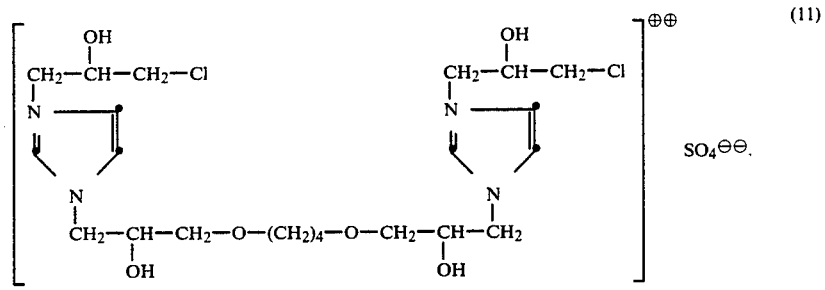

The starting bisimidazole of formula (II) is prepared as follows:

41 g of 2-methylimidazole are dissolved in 88.5 g of water and the resultant solution is warmed to 45° C. Then 54.5 g of butanediol diglycidyl ether are added dropwise over 15 minutes, the temperature rising to 60° C. The reaction mixture is stirred for 25 minutes at this temperature, affording 184 g of a clear 52% solution of the bisimidazole of formula (II). The epoxide content is 0.

EXAMPLE 3

153.3 g of a bisimidazole (50% in water) of the formula

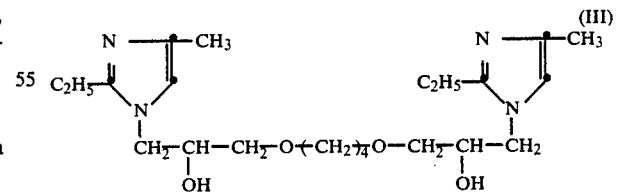

are mixed with 9 g of 96% sulfuric acid and 23.5 g of water. Then 32.4 g of epichlorohydrin are added dropwise to the solution so obtained, the temperature rising to about 70° C. The reaction mixture is subsequently stirred for 4 hours at 70, after which time the amine number and epoxy number are both 0. The solution is evaporated to dryness, affording 117 g of a bisimidazolium salt of the formula

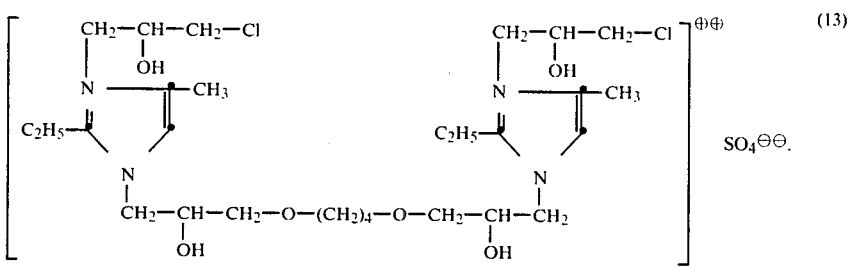

(13)

The starting bisimidazole of formula (III) is prepared as follows:

38.5 g of 2-ethyl-4-methylimidazole are dissolved in 76.65 g of water and the resultant solution is warmed to 55° C. Then 38.2 g of butanediol diglycidyl ether are added dropwise over 15 minutes, the temperature rising to 62° C. The reaction mixture is stirred for 1 hour at this temperature, affording 153.3 g of a clear 50% solution of the bisimidazole of formula (III). The epoxide content is 0.

EXAMPLE 4

195.6 g of a bisimidazole (45% in water) of the formula

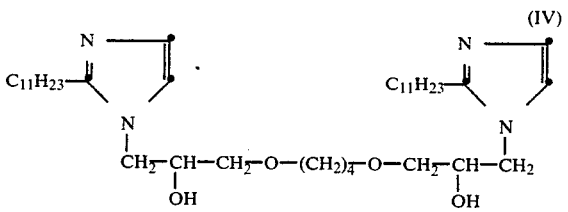

are mixed with 7 g of 96% sulfuric acid and 18.6 g of water. Then 25.6 g of epichlorohydrin are added dropwise at 60° C. to the solution so obtained, the temperature rising to about 70° C. The reaction mixture is subsequently stirred for 3½ hours at 70°–75° C., after which time the amine number and epoxy number are both 0. The solution is evaporated to dryness, affording 120 g of a bisimidazolium salt of the formula The starting bisimidazole of formula (IV) is prepared as follows:

57.6 g of undecylimidazole are dissolved in 87.8 g of water and 20 g of isopropanol and the resultant solution is warmed to 60° C. Then 30.2 g of butanediol diglycidyl ether are added dropwise over 15 minutes, the temperature rising to 65° C. The reaction mixture is stirred for 2 hours at this temperature, affording 195.6 g of a slightly turbid 45% solution of the bisimidazole of formula (IV). The epoxide content is 0.

EXAMPLE 5

225 g of a bisimidazole (50% in water) of the formula

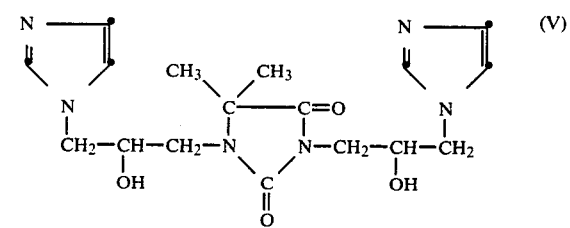

are mixed with 12.7 g of 96% sulfuric acid and 33.5 g of water. Then 46.25 g of epichlorohydrin are added dropwise at 60° C. to the solution so obtained, the temperature rising to 68° C. The reaction mixture is subsequently stirred for 10 hours at 70°–75° C., after which time the amine number and epoxy number are both 0. The solution is evaporated to dryness, affording 170 g of a bisimidazolium salt of the formula

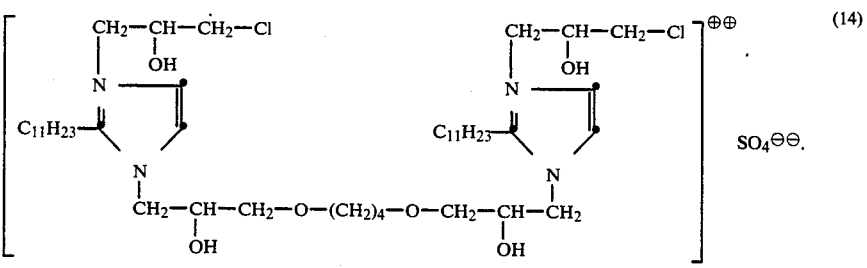

(14)

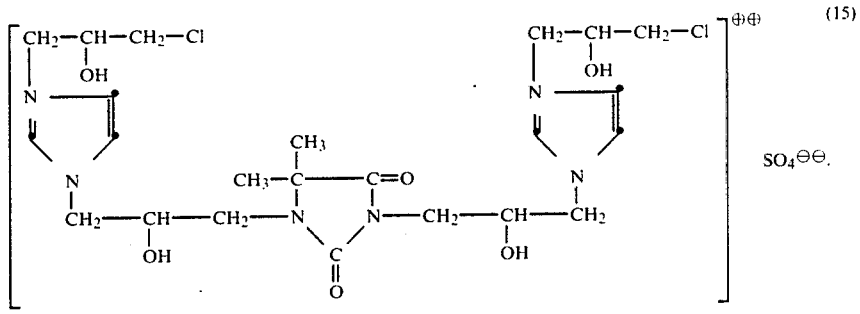

The starting bisimidazole of formula (V) is prepared as follows:

34 g of imidazole are dissolved in 112.5 g of water and the resultant solution is warmed to 45° C. Then 78.5 g of a bisepoxide of the formula are mixed with 6.38 g of 96% sulfuric acid and 28.2 g of water. Then 23.2 g of epichlorohydrin are added dropwise at 60° C. to the solution so obtained, the temperature rising to 71° C. The reaction mixture is subsequently stirred for 12 hours at 70°–75° C., after which time the amine number and epoxy number are both 0. The solution is evaporated to dryness, affording 92.2 g of a bisimidazolium salt of the formula

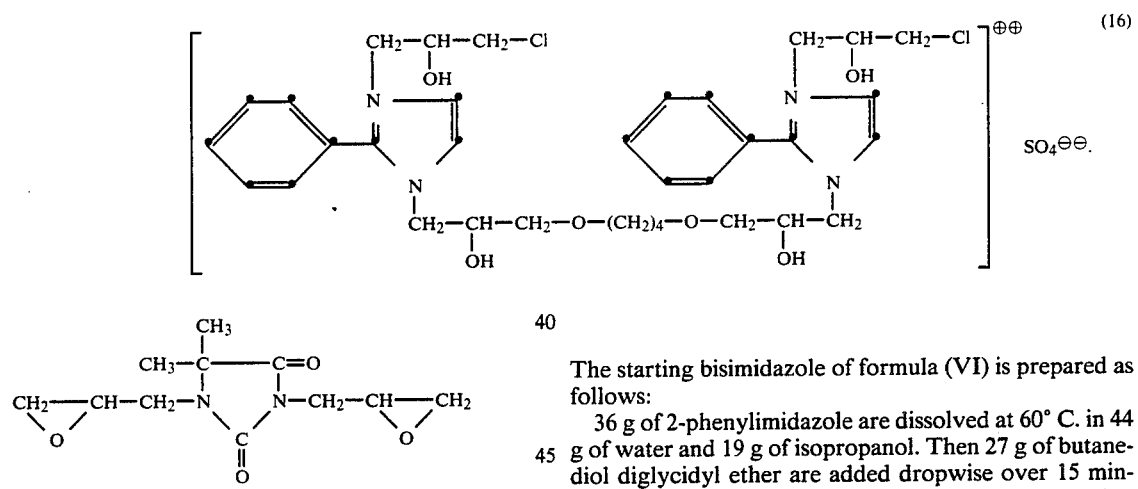

ether are added dropwise, the temperature rising to 61° C. After a reaction time of 70 minutes at 60° C., the epoxide content is 0. Yield: 225 g of a clear 50% solution of the bisimidazole of formula (V).

EXAMPLE 6

126 g of a bisimidazole (50% in a 7:3 mixture of water/ isopropanol) of the formula The starting bisimidazole of formula (VI) is prepared as follows:

36 g of 2-phenylimidazole are dissolved at 60° C. in 44 g of water and 19 g of isopropanol. Then 27 g of butanediol diglycidyl ether are added dropwise over 15 minutes, the temperature rising to 68° C. After a reaction time of 30 minutes at 70° C., the epoxide content is 0. Yield: 126 g of a 50% solution of the bisimidazole of the formula (VI).

USE EXAMPLES

EXAMPLE 1

500 g of cotton yarn are wetted in 5 liters of water in a cheese dyeing machine and the liquor is then heated to 95°–98° C. Then 20 g of a dye of the formula

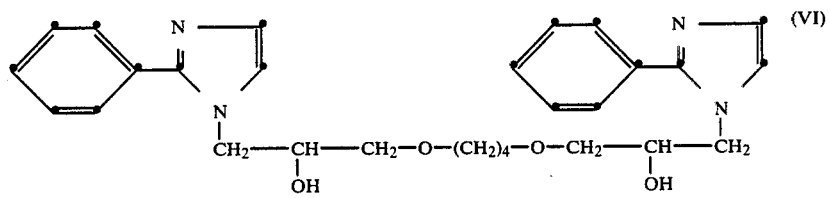

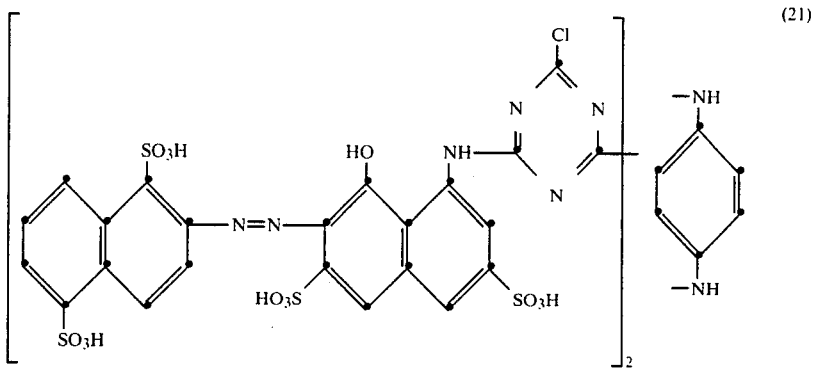
(21)

and 400 g of sodium sulfate are added. After cooling to 80° C., 10 ml of an aqueous 30% sodium hydroxide solution and 25 g of sodium carbonate are added. The dye bath is further cooled to 40° C. and 60 ml of 30% aqueous sodium hydroxide solution and 50 g of the bisimidazolium sulfate prepared according to Example 1 are added. The cotton fabric is treated for a further 60 minutes at 40° C. and then rinsed and dried.

A level, strong red dyeing of increased colour yield and with excellent wetfastness properties is obtained. The ISO C2S wash is appreciably improved.

EXAMPLE 2

100 g of cotton fabric are wetted in 800 g of water in a short liquor jet dyeing apparatus. The bath is then warmed to 40° C. and 3 g of a direct dye of the formula

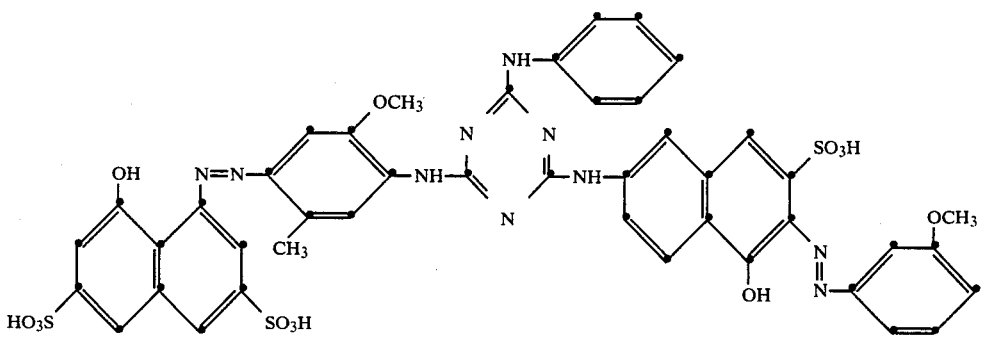
(22)

and 48 g of sodium sulfate are added. After 10 minutes, 9.6 g of an aqueous 30% sodium hydroxide solution and 8 g of the bisimidazolium sulfate prepared according to Example 1 are added at the same temperature. The cotton fabric is then treated for 60 minutes at 40° C. and then rinsed and dried.

A level, strong red dyeing with a 50% increase in yield is obtained. The ISO C2S wash has a rating of 4.

EXAMPLE 3

A cotton fabric is impregnated on a pad with a liquor which contains
60 g/l of the dye of the formula

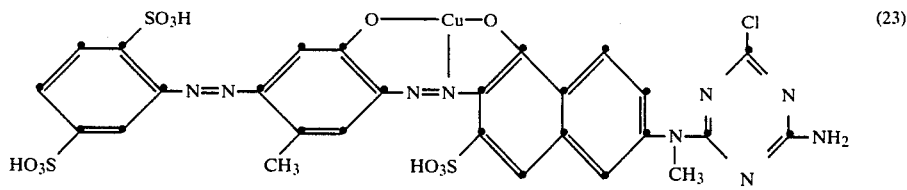
(23)

100 g/l of urea
35 g/l of the bisimidazolium sulfate prepared according to Example 1
40 g/l of 30% sodium hydroxide solution and
3 g/l of the sodium salt of 3-nitrobenzenesulfonic acid. The liquor pick-up is 80%. The fabric is then rolled up and stored for 18 hours at room temperature, then washed hot and cold and dried.

The strong, level blue dyeing so obtained exhibits a 20% improvement in colour yield. After storage for 3 days at 60° C. in a saturated steam atmosphere, the dyeing causes no staining of the adjacent fabric (hydrolysis test before the ISO C2S wash). The ISO C2S wash also has the rating 4 after the hydrolysis test.

EXAMPLE 4

Cotton tricot is padded with a liquor which contains 12 g/l of the dye of the formula

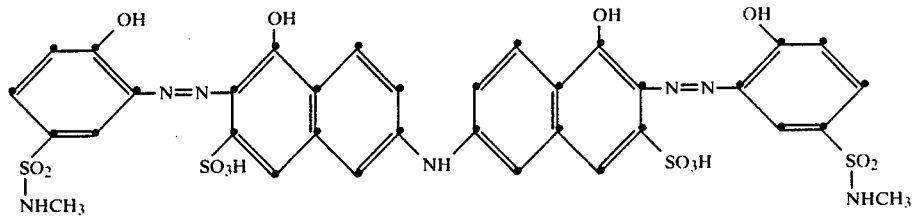
(24)

100 g/l of urea
35 g/l of 30% sodium hydroxide solution
26 g/l of the bisimidazolium sulfate prepared according to Example 1.

The cotton fabric is then rolled up, packed airtight and stored for 20 hours at room temperature. The goods are afterwards rinsed and dried. The increase in yield of the strong violet dyeing so obtained is 100% and, in addition, the wetfastness properties of the dyeing are excellent. There is virtually no staining of the adjacent fabric in the ISO C2S wash test and in the test for fastness to wet pressing.

EXAMPLE 5

A dyeing which has been produced on cotton tricot with 6% of the dye of formula (21) is padded to a pick-up of 85% with a liquor which contains
26 g/l of the bisimidazolium sulfate prepared according to Example 1 and
32 ml/l of 30% sodium hydroxide solution.

The goods are afterwards dried at 90° C. and then treated for 3 minutes at 140° C. The cotton fabric is subsequently rinsed and dried.

After a hydrolysis test, the fabric has the rating 4 in the ISO C2S wash test.

EXAMPLE 6

A dyeing which has been obtained in conventional manner with 5% of the dye of the formula 26 g/l of the bisimidazolium sulfate prepared according to Example 1 and
32 ml/l of 30% sodium hydroxide solution.

The goods are then dried at 90° C. and subjected to a thermosol fixation at 140° C.

1 kg of the pretreated fabric is wetted in 30 liters of water at 25° C. and then 30 g of a dye of the formula

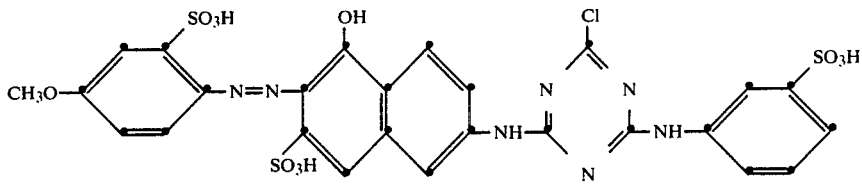
(16)

600 g of sodium carbonate and 90 ml of 30% sodium hydroxide solution are added.

The dye liquor is heated to 80° C. over 40 minutes and kept at this temperature for 60 minutes. The dyed fabric is subsequently rinsed hot and cold and dried.

The pretreatment of the fabric with the bisimidazolium salt improves the dye yield by 60%. In addition, the dyeing has excellent wetfastness properties.

EXAMPLE 8

Bleached cotton terry is printed on a cylinder printing machine with 1 kg of a printing paste composed of
400 g of 5% alginate thickener
100 g of urea
50 g of a dye of the formula (27)

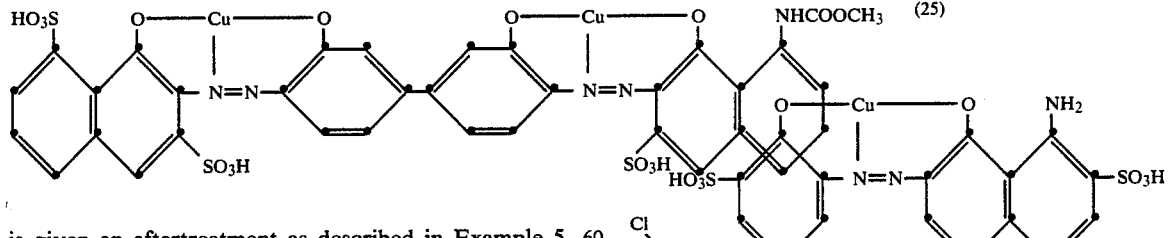
(25)

is given an aftertreatment as described in Example 5. Compared with a dyeing which has been aftertreated in conventional manner, there is no staining of the adjacent fabric in the tests for the ISO C2S wash and for fastness to wet pressing.

EXAMPLE 7

A cotton fabric is padded, before dyeing, with a liquor which contains 10 g of sodium m-nitrobenzenesulfonate
60 g of 30% sodium carbonate solution and 380 g of water
such that 3 cm printed stripes alternate with 3 cm unprinted stripes. The printed fabric is then dried, steamed for 8 minutes at 101° C., rinsed, soaped at the boil and dried. The printed fabric is then padded to a pick-up of 85% with a liquor which contains 23 g/l of the bisimidazolium sulfate prepared according to Example 1 and 30 ml/l of 30% sodium hydroxide solution.

The fabric is then dried at 80° C. and treated for 3 minutes at 140° C., and subsequently rinsed and dried. The wetfastness properties, especially the ISO C2S wash and the fastness to wet pressing, are appreciably improved by this aftertreatment with the imidazolium salt, and also after a hydrolysis test.

Strong and level dyeings and prints with improved colour yield and excellent wetfastness properties are likewise obtained by using in Examples 1 to 8 the same amount of a bisimidazolium salt prepared according to Examples 2 to 6 instead of the bisimidazolium sulfate prepared according to Example 1.

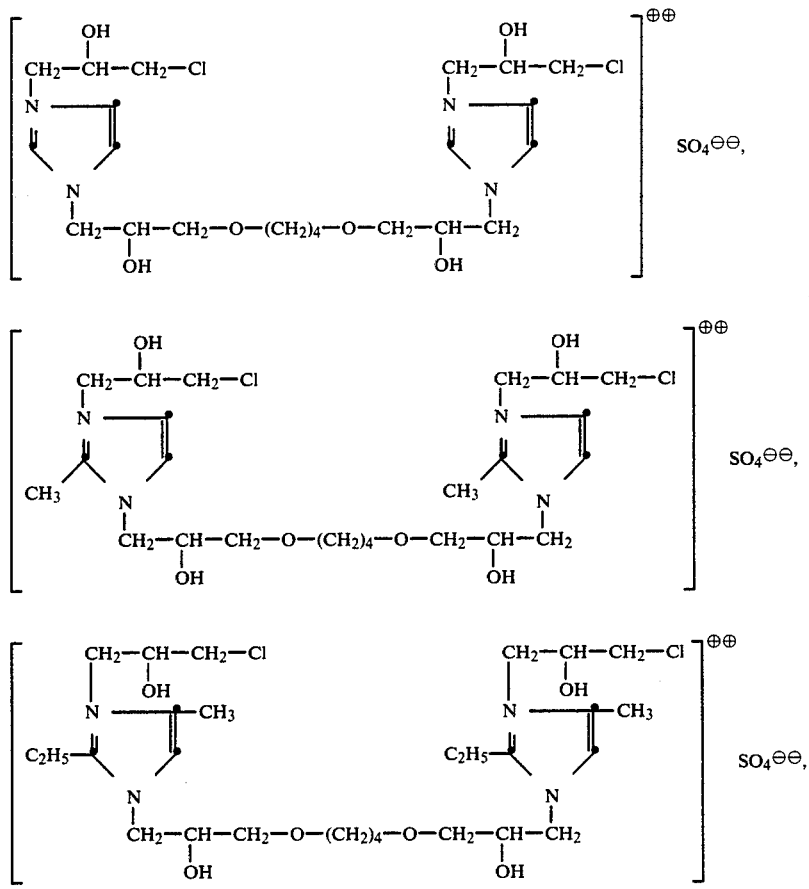

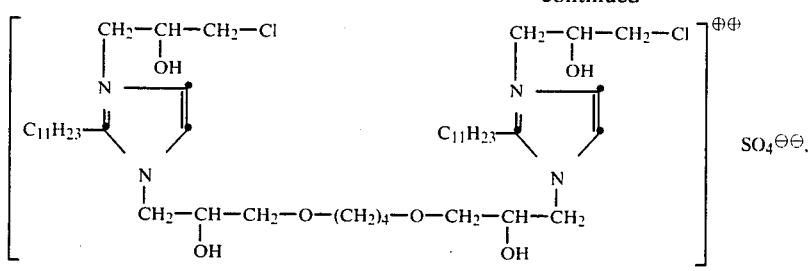
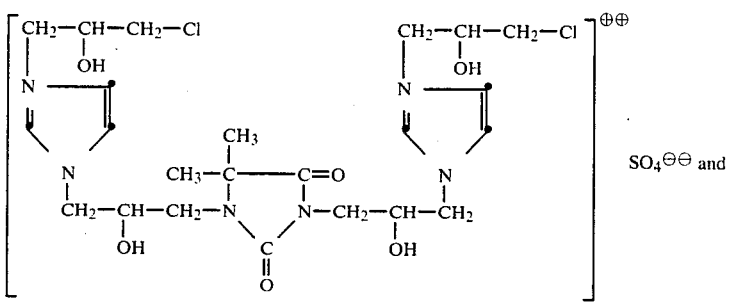
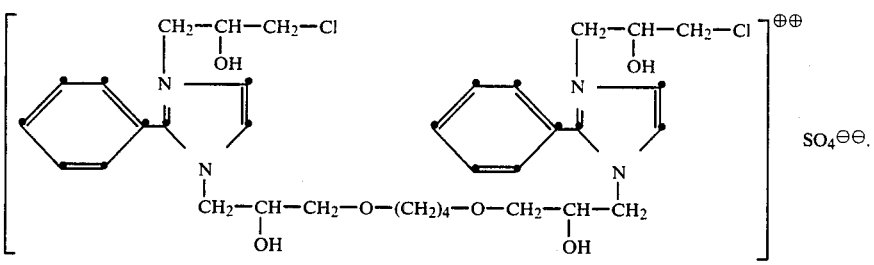

What is claimed is:

1. A bisimidiazolium salt of the formula

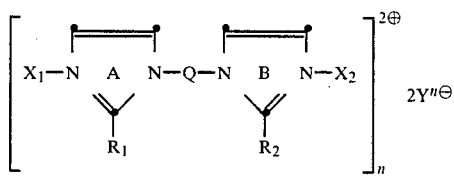

(1)

wherein

Q is a divanet aliphatic hydrocarbon radical of 4 to 12 carbon atoms, which is unsubstituted or substituted by hydroxyl groups and which may be interrupted in the chain by oxygen or by a hydrantoin group, $X_1$ and $X_2$, each independently of the other, are the

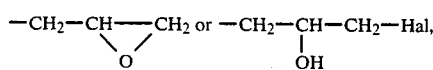

Hal is halogen, $R_1$ and $R_2$, each independently of the other, are hydrogen, phenyl or an aliphatic radical having 1 to 23 carbon atoms, n is 1 or 2, and $Y^\ominus$ is an anoin of a strong inorganic or organic acid, and the imidazole rings A and B, each independently of the other, are unsubstituted or substituted by lower alkyl which is in turn unsubstituted or substituted by halogen, hydroxyl or cyano.

2. A bisimidazolium salt according to claim 1, wherein $X_1$ and $X_2$ are halohydrin groups of the formula

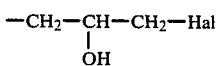

wherein Hal is bromine or chlorine.

3. A bisimidazolium salt according to claim 1, wherein $R_1$ and $R_2$ are hydrogen, phenyl or $C_1$-$C_{17}$-alkyl.

4. A bisimidzaolium salt according to claim 3, wherein $R_1$ and $R_2$ are hydrogen, phenyl, lower alkyl, undecyl or heptadecyl.

5. A bisimidazolium salt according to claim 1, wherein Q is a $C_6$-$C_{10}$alkylene radical which is unsubstituted or substituted by hydroxyl groups and which may be interrupted in the chain by oxygen or by a hydrantoin group which is attached through the N-atoms and is unsubstituted or substituted in the $\alpha$-position by methyl.

6. A bisimidazolium salt according to claim 5, wherein Q is a $C_6$-$C_{10}$alkylene radical which is interrupted by oxygen and is unsubstituted or substituted by hydroxyl groups.

7. a bisimidazolium salt of the formula

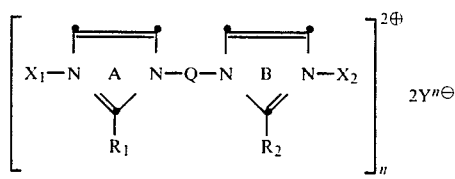

wherein

Q is a divalent aliphatic hydrocarbon radical of 4 to 12 carbon atoms, which is bound to the imidazole radicals by carbon atoms, which is unsubstituted or substituted by 1 or 2 hydroxyl groups and which may be interrupted in the chain by 1 or 2 oxygen atoms or by one hydrantoin group which is bound into Q by its N-atoms and which may be substituted in the alpha-position by one or two lower alkyl groups;

$X_1$ and $X_2$, each independently of the other, are

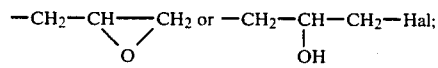

Hal is halogen;

$R_1$ and $R_2$, each independently of the other, are hydrogen, phenyl or an aliphatic radical having 1 to 23 carbon atoms;

n is a 1 or 2; and $Y^\ominus$ is an anion of a strong inorganic or organic acid, and the imidazole rings A and B, each independently of the other, are unsubstituted or substituted by lower alkyl which is in turn unsubstituted or substituted by halogen, hydroxyl or cyano.

8. A bisimidazolium salt according to claim 7, wherein $X_1$ and $X_2$ are halohydrin groups of the formula

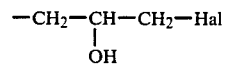

wherein Hal is bromine or chlorine.

9. A bisimidazolium salt according to claim 7, wherein $R_1$ and $R_2$ are hydrogen, phenyl or $C_1$-$C_{17}$-alkyl.

10. A bisimidazolium salt according to claim 9, wherein $R_1$ and $R_2$ are hydrogen, phenyl, lower alkyl, undecyl or heptadecyl.

11. A bisimidazolium salt according to claim 7, wherein Q is a $C_6$-$C_{10}$alkylene radical which is unsubstituted or substituted by hydroxyl groups and which may be interrupted in the chain by 1 or 2 oxygen atoms or by a hydantoin group which is attached through the N-atoms and is unsubstituted or substituted in the alpha-position by methyl.

12. A bisimidazolium salt according to claim 11, wherein Q is a $C_6$-$C_{10}$alkylene radical which is interrupted by 2 oxygen atoms and is substituted by two hydroxyl groups.

13. A bisimidazolium salt according to claim 7, of the formula

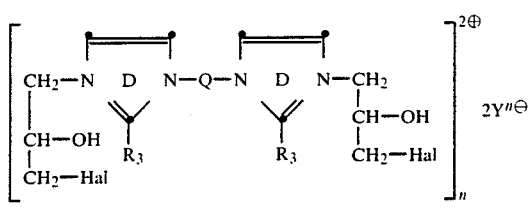

wherein
 n and $Y^\ominus$ are as defined in claim 7,
 Hal is bromine or chlorine,
 Q is a $C_6$-$C_{10}$alkylene radical which is unsubstituted or substituted by hydroxyl groups and which may be interrupted in the chain by oxygen or by a hydrantoin group which is attached through the N-atoms and is unsubstituted or substituted in the α-position by methyl, and $R_3$ is hydrogen, phenyl or $C_1$-$C_{17}$alkyl,
and the ring D is unsubstituted or substituted by methyl or ethyl.

14. A bisimidazolium salt according to claim 7, of the formula

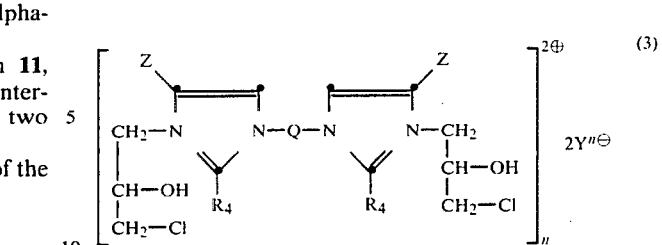

wherein
 Q is a $C_6$-$C_{10}$alkylene radical which is unsubstituted or substituted by hydroxyl groups and which may be interrupted in the chain by oxygen or by a hydantoin group which is attached through the N-atoms and is substituted in the α-position by methyl,
 $R_4$ is hydrogen, phenyl or $C_1$-$C_{11}$alkyl,
 Z is hydrogen or methyl,
 n is 1 or 2, and
 $Y^\ominus$ is the chloride or sulfate ion.

15. A bisimidazolium salt according to claim 14, wherein Q is a $C_6$-$C_{10}$alkylene radical which is substituted by hydroxyl groups and which is interrupted in the chain by oxygen,
 $R_4$ is hydrogen or methyl,
 Z is hydrogen,
 n is 1 or 2, and
 $Y^\ominus$ is the chloride or sulfate ion.

16. A bisimidazolium salt according to claim 7 selected from the group consisting of: